(12) United States Patent
Chitre et al.

(10) Patent No.: US 6,430,448 B1
(45) Date of Patent: Aug. 6, 2002

(54) STIMULATING ELECTRODE HAVING LOW POLARIZATION AND METHOD OF MAKING SAME

(75) Inventors: Yougandh Chitre; Phong Doan, both of Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 81 days.

(21) Appl. No.: 09/707,828

(22) Filed: Nov. 7, 2000

(51) Int. Cl.⁷ ................................................. A61N 1/06
(52) U.S. Cl. ....................................... 607/121; 607/119
(58) Field of Search ............................ 607/9, 115, 116, 607/119, 121, 122; 606/32; 600/374, 375

(56) References Cited

U.S. PATENT DOCUMENTS

| | | | |
|---|---|---|---|
| 3,749,101 A | 7/1973 | Williamson | 128/418 |
| 4,281,668 A | 8/1981 | Richter et al. | 128/784 |
| 4,352,360 A | 10/1982 | King | 128/786 |
| 4,502,492 A | 3/1985 | Bornzin | 128/785 |
| 5,074,313 A | 12/1991 | Dahl et al. | 128/784 |
| 5,143,089 A | 9/1992 | Alt | 128/784 |
| 5,143,090 A * | 9/1992 | Dutcher et al. | 607/121 |
| 5,181,526 A | 1/1993 | Yamasaki | 128/784 |
| 5,217,028 A * | 6/1993 | Dutcher et al. | 607/122 X |
| 5,255,693 A * | 10/1993 | Dutcher et al. | 607/120 |
| 5,385,579 A * | 1/1995 | Helland | 607/130 |
| 5,534,022 A * | 7/1996 | Hoffmann et al. | 607/119 X |
| 5,628,778 A | 5/1997 | Kruse et al. | 607/123 |
| 5,645,580 A * | 7/1997 | Moaddeb et al. | 607/122 |
| 5,755,762 A | 5/1998 | Bush | 607/122 |
| 5,824,016 A | 10/1998 | Ekwall | 607/9 |
| 5,851,896 A | 12/1998 | Summerfelt | 438/396 |
| 5,931,862 A | 8/1999 | Carson | 607/120 |
| 5,935,158 A * | 8/1999 | Holmstrom et al. | 607/116 |
| 6,253,110 B1 * | 6/2001 | Brabec et al. | 607/116 |

OTHER PUBLICATIONS

Schaldach, "The Stimulating Electrode", *Electrotherapy of the Heart*, Spr–Vlg, pp 145–168, (1992).

De Voogt, Willem G., M.D., "Pacemaker Leads: Performance and Progress", The American Journal of Cardiology, vol. 83 (5B), pp 187D–191D, (Mar. 11, 1999).

* cited by examiner

*Primary Examiner*—John Rivell

(57) ABSTRACT

An implantable stimulating electrode for directly contacting the endocardium of a human heart exhibits low polarization values of less than about 0.3 mV and is intended for use with an implantable lead having an electrical connector coupled to the proximal end of a conductor for releasable attachment to a stimulating pulse generator. The electrode is comprised of a metallic substrate having an initially exposed outer surface substantially covered with a first inner layer of titanium nitride and a second outer layer of platinum black. The first inner layer of titanium nitride has a thickness of less than about 15 microns and the second outer layer of platinum black overlying the layer of titanium nitride, similarly, has a thickness of less than about 15 microns. The invention includes a method of making the implantable stimulating electrode.

5 Claims, 3 Drawing Sheets

STIMULATING ELECTRODE HAVING LOW POLARIZATION AND METHOD OF MAKING SAME

FIELD OF THE INVENTION

The present invention relates generally to lead assemblies for connecting implantable medical devices with selected body tissue to be stimulated by such devices, and more particularly to a stimulating electrode for use with such lead assemblies having low polarization which results in lower capture thresholds, increased sensing thresholds, and clearer evoked response signals.

BACKGROUND OF THE INVENTION

Polarization, is an artifact that results from the accumulation of charge at the electrode/tissue interface post-stimulation. This after-potential prevents the accurate sensing of intrinsic cardiac electrical activity.

Current electrodes, both of the tip and ring variety, of modern pacing leads often employ a surface coating of titanium nitride (TiN). The implementation of TiN as a coating material of choice earlier provided a breakthrough in the pacing industry by exhibiting properties of corrosion resistance and providing an interface with increased electrode/tissue capacitance. The increase in interface capacitance is a result of the increased active surface area brought about by the fractal morphology of the sputter coated titanium nitride material. The increase in interface capacitance, in turn, lowers the polarization artifact typically seen following the pacing pulse. This falls out from the equation describing the after-potential or polarization given by equation (1), as follows.

$$U_C(t > T) = U_r \left(1 - \exp\left(\frac{-T}{R_L C_H}\right)\right) \exp\left(\frac{-(t-T)}{R_L C_H}\right) \quad (1)$$

where:
- $R_L$: resistance of the lead
- $C_H$: Helmholtz capacitance
- $U_r$: charge voltage Although the lowering of the polarization value can be achieved by increasing the lead length, which in turn increases $R_L$, the resistance of the lead, it compromises the sensing functionality of the electrode and increases energy consumption. See Schaldach, "The Electrode-Electrolyte Interface", *Electrotherapy of the Heart*, Spr-Vlg, 1992.

There are numerous disclosures of known leads and associated stimulating electrodes presented in the patented format. A number of the more pertinent known disclosures will now be discussed.

General disclosures of body implantable electrode constructions in which either or both of the leads and electrodes are constructed of titanium or titanium alloy are found in U.S. Pat. No. 5,181,526 to Yamasaki, U.S. Pat. No. 5,074,313 to Dahl et al. and U.S. Pat. No. 4,352,360 to King. In another instance as disclosed in U.S. Pat. No. 5,931,862 to Carson and U.S. Pat. No. 5,755,762 to Bush, a continuous sheath of open-celled porous plastic, preferably ePTFE, is used on the outside of a medical lead, extending along the lead body and the electrodes. Because the plastic is open-celled, when the pores are filled with saline, the lead can deliver electrical energy through the pores in the plastic. Pore size is chosen to discourage tissue ingrowth while allowing for defibrillation energy delivery and electrical signals through it. U.S. Pat. No. 5,824,016 to Ekwall discloses an implantable medical device for stimulating tissue including a pulse generator and associated electrode designed to prevent leakage currents in the output circuit. This is said to be accomplished by utilization of the electrode lead-to-tissue electrolytic interface capacitance (Helmholtz capacitance) with a highly leakage resistant layer interface together with and formed, for example, by titanium and titanium dioxide. U.S. Pat. No. 3,749,101 to Williamson discloses, without mention of, or concern for, polarization or Helmholtz capacitance, an electrode for muscle stimulation featuring a platinum electrode which has preferably been platinized to develop a coating of platinum black, contained in a second electrode housing of suitable electrode metal which is compatible with platinum such as titanium. Finally, the present invention recognizes that the use of a platinum black coating with materials other than titanium have long been known to reduce source impedance and polarization. See, for example, U.S. Pat. No. 5,628,778 to Kruse et al., col. 6, line 66 through col. 7, line 21. Indeed, the use of a platinum black coating even with titanium has long been known to reduce source impedance and polarization, witness U.S. Pat. No. 4,502,492 to Bornzin at col. 3, lines 57 through 65. Yet another noteworthy disclosure is presented in U.S. Pat. No. 5,851,896 to Summerfelt, which is concerned with providing a barrier layer for use in a high-dielectric constant material electrode. The barrier layer is defined as a conductive layer which minimizes diffusion of oxygen through itself down to the oxidizable layer, thus minimizing oxidation and degradation of the oxidizable layer. A preferred embodiment comprises an oxidizable layer (e.g. TiN), a conductive exotic-nitride barrier layer (e.g. Ti—Al—N) overlying the oxidizable layer, an oxygen stable layer (e.g. platinum) overlying the exotic-nitride layer, and a high-dielectric-constant material layer (e.g. barium strontium titanate) overlying the oxygen stable layer.

It was with knowledge of the foregoing state of the technology that the present invention has been conceived and is now reduced to practice.

SUMMARY OF THE INVENTION

The present invention, then, relates to an implantable stimulating electrode for directly contacting the endocardium of a human heart and exhibiting low polarization values (of less than about 0.3 mV). The stimulating electrode is intended for use with an implantable lead having an electrical connector coupled to the proximal end of a conductor for releasable attachment to a stimulating pulse generator. The electrode is comprised of a metallic substrate having an initially exposed outer surface substantially covered with a first inner layer of titanium nitride and a second outer layer of platinum black. The first inner layer of titanium nitride has a thickness of less than about 15 microns and the second outer layer of platinum black overlying the layer of titanium nitride, similarly, has a thickness of less than about 15 microns. The invention also includes a method of making the implantable stimulating electrode.

A more viable approach than increasing lead length, as earlier mentioned, and as presented herein, is to alleviate the polarization artifact by maximizing the Helmholtz capacitance, CH. The lowering of the after-potential or polarization artifact has a two-fold purpose:

(1) in conjunction with low-threshold leads, it decreases battery consumption; and (2) it allows capture detection and, therefore, safer pacing at low battery consumption.

See, for example, de Voogt, W. G., "Pacemaker Leads: Performance and Progress", *American Journal of Cardiology*, 1999 Mar., 83:5B, pages 187D–191D.

However, materials such as titanium have the propensity to oxidize readily in the atmosphere. For example, for a material such as titanium nitride, the ratio of final $TiO_2$ thickness to initial TiN thickness is about 1.58. See U.S. Pat. No. 5,851,896 to Summerfelt. The thin insulating or semi-conducting oxide layer amounts to a capacitor in series with the Helmholtz capacitance ($C_H$), thereby reducing the overall effective capacitance.

FIG. 1 depicts the equivalent circuit of an oxidizable interface as explained by Schaldach ("The Electrode-Electrolyte Interface", *Electrotherapy of the Heart*, Spr-Vlg, 1992), where:

$R_L$: resistance of the lead
$C_{OX}$: capacitance associated with the oxide layer
$R_{OX}$: resistance of the oxide layer
$R_F$: Faradaic resistance
$C_H$: Helmholtz capacitance $$C_{Eff} = \frac{(C_{OX})(C_H)}{C_{OX} + C_H} \quad (2)$$

$$C_{EFF} = C_H \left( \frac{C_{OX}}{C_{OX} + C_H} \right)$$

But:

$$C_{OX} < C_H$$

Therefore, $$\left( \frac{C_{OX}}{C_{OX} + C_H} \right) < 1$$

It follows from (2), that:

$$C_{EFF} < C_H$$

A primary feature, then, of the present invention is the provision of a stimulating electrode for use with an associated lead assembly having low polarization which results in lower capture thresholds, increased sensing thresholds, and clearer evoked response signals.

Another feature of the present invention is the provision of such a stimulating electrode exhibiting a polarization value of less than about 0.3 mV and for which the polarization value of an associated implantable lead is less than about one mV.

Still another feature of the present invention is the provision of such a stimulating electrode imparted with a layer of titanium nitride having a thickness of less than about 15 microns and with a layer of platinum black overlying the layer of titanium nitride having a thickness of less than about 15 microns.

Yet another feature of the present invention is the provision of such a stimulating electrode made by a method comprising the steps of, first, providing a blank metallic electrode having an outer surface substantially covered with a layer of titanium nitride, then immersing the blank electrode in an electroplating electrolyte solution comprised of chloroplatinic acid or an equivalent solution and then applying an emf across the volume of the electroplating electrolyte solution to thereby apply a coating of platinum black to the outer surface of the blank electrode resulting in a processed electrode.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 3A is an enlarged detail cross section view of the tip end of the lead body illustrated in FIG. 3;

DETAILED DESCRIPTION OF THE INVENTION

Figure 1:
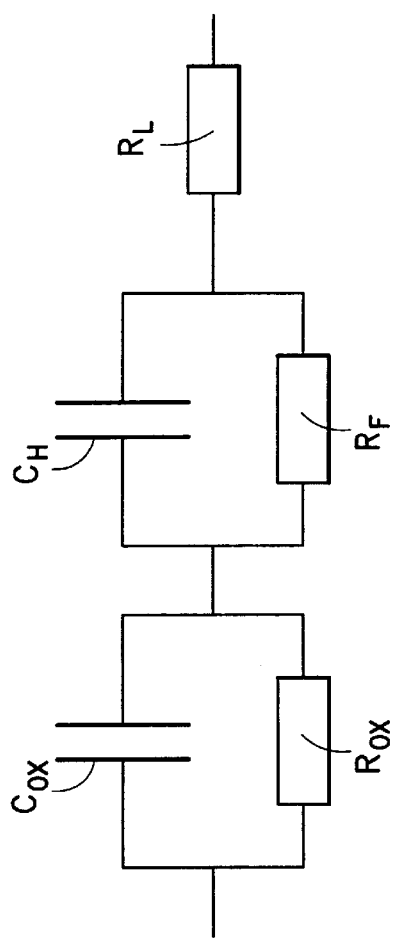
FIG. 1 is a schematic view of an electrical circuit depicting the equivalent circuit of an oxidizable interface.
Figure 2:
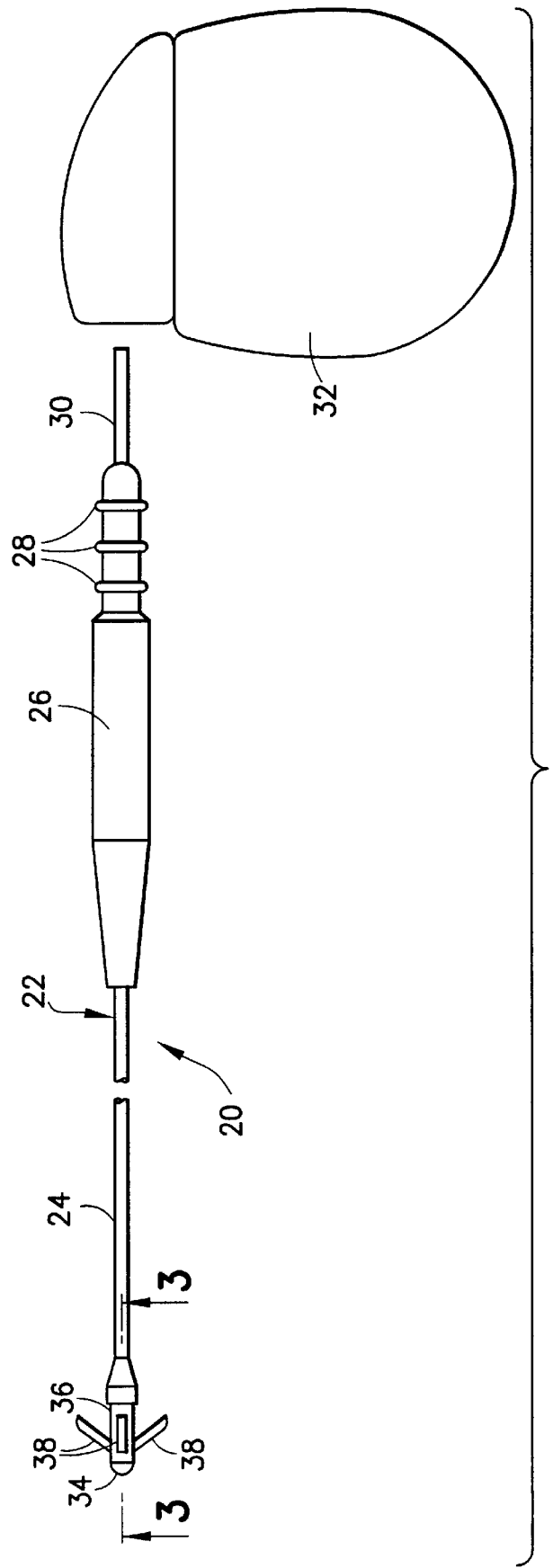
FIG. 2 is an exploded side elevation view of a tissue stimulating system embodying the present invention.

Referring now to FIG. 2, there is shown an exploded side elevation view of a tissue stimulating system 20 incorporating features of the present invention. Although the present invention will be described with reference to the embodiment shown in the drawings, it should be understood that the present invention can be embodied in many alternate forms or embodiments. In addition, any suitable size, shape or type of elements or materials could be used.

The tissue stimulating system 20 includes an elongated lead body 22 which is covered with an insulation sheath 24 fabricated of silicone rubber, polyurethane, or other suitable plastic material. A connector assembly 26 located at the proximal end of the lead body 22 is provided with sealing rings 28 and carries a connector pin 30 for connection in a known manner with a suitable stimulating pulse generator 32. The connector assembly 26 may be constructed using known techniques and may be fabricated of silicone rubber, polyurethane, or other suitable plastic material. Connector pin 30 may be fabricated of stainless steel or other conductive material.

At the distal end of the lead body 22 is a stimulating electrode 34 and immediately proximal to the exposed portion of the electrode 34 is a tine sheath 36 which bears a plurality of circumferentially spaced tines 38. The tines 38 engage with heart tissue and urge electrode 34 into engagement with the endocardium in a direction generally parallel to the axis of the lead body 22.

Figure 3:
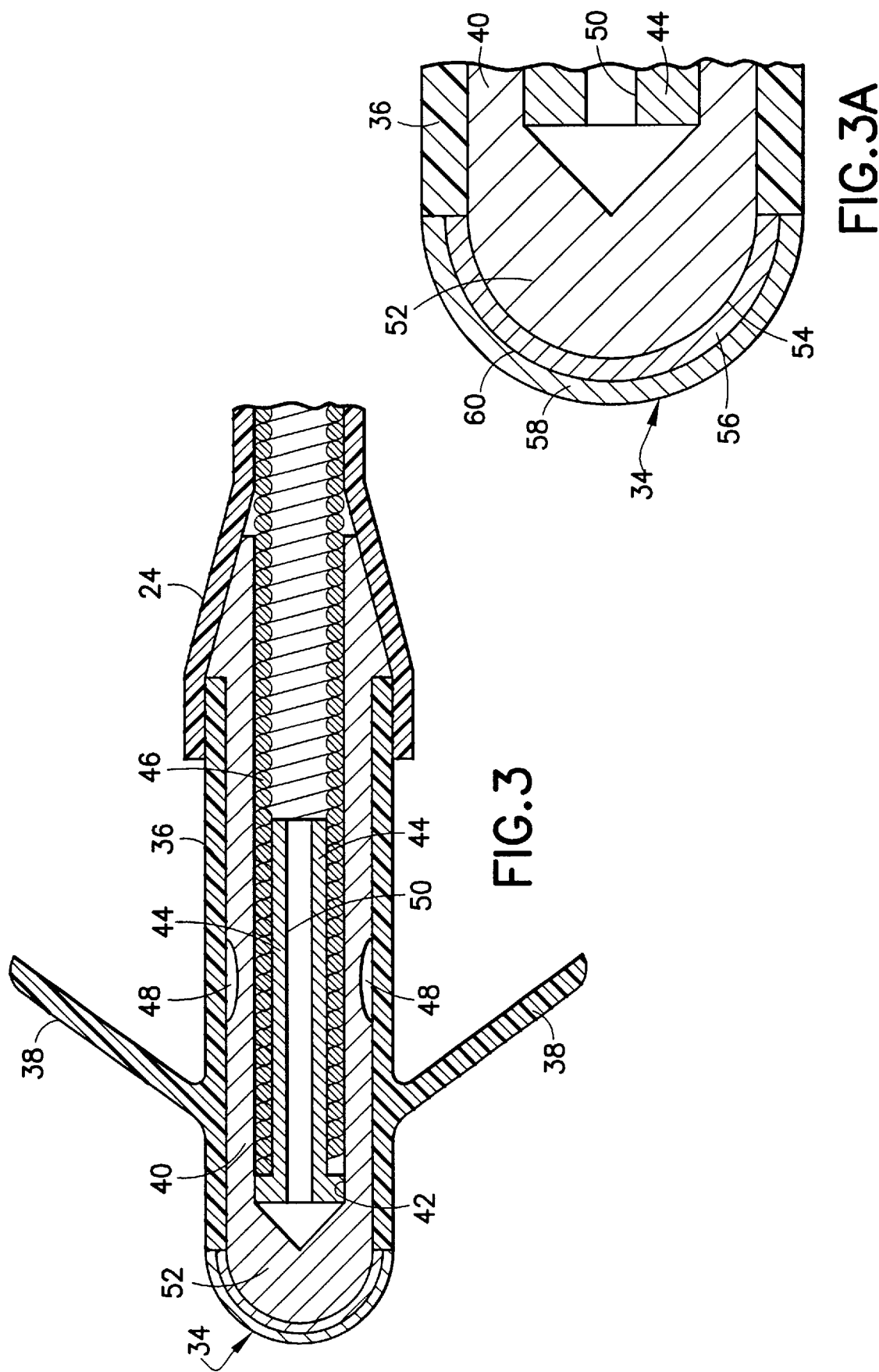
FIG. 3 is a cross sectional view taken generally along line 3—3 in FIG. 2.

FIG. 3 illustrates a cross sectional view of the electrode 34 shown in FIG. 2. In this view, electrode 34 is seen to be provided with an elongated tubular portion 40, which has a central lumen 42. Mounted within lumen 42, in a typical construction, are swaging pin 44 and coiled conductor 46. Crimps 48 maintain the coiled conductor 46 tightly fixed between the swaging pin 44 and the tubular portion 40 of electrode 34. This structure provides mechanical and electrical coupling of conductor 46 to electrode 34. The coiled conductor 46 extends proximal within the insulating sheath 24 to the proximal end of the lead body 22 and is coupled to connector pin 30. The swaging pin 44 is provided with a central lumen 50 into which a stylet may be inserted. The coiled conductor may be fabricated of MP35N alloy or other suitable conductive material and is preferably a multifilar coil. Swaging pin 44 may be fabricated of stainless steel or other appropriate metal. The substrate portion 52 of electrode 34 may be constructed, for example, of platinum, titanium, rhodium, iridium, or alloys of those metals, or of any of the platinum iridium alloys. Also, while the electrode 34 is illustrated as a tip electrode, the invention is just as applicable to a ring electrode of known design spaced proximally of the tip end of the lead body 22.

As best seen in FIG. 3A, an enlarged detail view of the tip end of the lead body 22 illustrated in FIG. 3, substantially all of the exposed surface 54 of the distal stimulating electrode 34, that is, the surface of the electrode extending distally of the tine sheath 36, is provided with an underlying layer 56 of titanium nitride and an overlying layer 58 of platinum black.

It is hypothesized that electroplating platinum black on a surface 60 (FIG. 3A) of TiN coated electrodes, more specifically ring electrodes and tip electrodes, of pacing leads alleviates the polarization artifact by a two step mechanism:
(1) the electroplating solution etches the existing layer of $TiO_2$; and
(2) the overlay of platinum black inhibits further oxidation of the TiN surface.

The following example serves to illustrate the present invention in the manner just presented but should not be considered to limit the scope of the invention.

EXAMPLE

Figure 4:
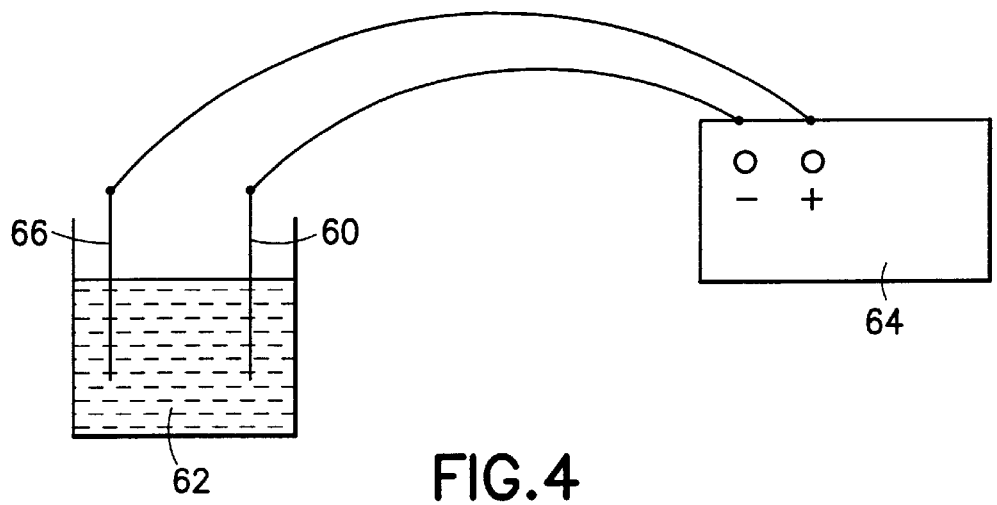
FIG. 4 is a schematic view depicting the electroplating operation for achieving the unique electrode construction of the invention.

Polarization amplitudes were quantified by a test fixture that employs a pacemaker hybrid. Other materials employed included a polarization test tank, a 0.9% saline solution, distilled water, and alcohol. Electrode surface 54 was electroplated following an established, documented procedure. More specifically, the following steps were carried out in the electroplating process:

1. handling the lead with gloves to minimize contamination;
2. inspecting the electrode surface 60 under a microscope;
3. cleaning the electrode surface 60 with acetone using a Q-tip;
4. blowing air on the electrode surface 60 to remove debris and contamination;
5. twice repeating the cleaning process of steps 3. and 4.:
6. dipping the electrode surface 60 in alcohol, then into a bath of electrolyte (FIG. 4), specifically, chloroplatinic acid;
7. plating the electrode surface 60 with platinum black (layer 58) resulting from an electrochemical plating reaction driven by a 12 v. power source (FIG. 4);
8. agitating the electrode surface during the plating process, retaining the electrode surface in the plating solution for about 45 seconds; 9. removing the processed electrode surface from the plating solution;
10. rinsing the processed electrode surface in distilled water;
11. dipping the processed electrode in acetone;
12. gently touching the processed electrode surface using a Q-tip to help check the adhesion of platinum black on the titanium nitride surface;
13. repeating the plating process a second time;
14. checking polarity to ensure the electrode surface is properly plated, not a reference electrode 66 (FIG. 4).

Figure 5:
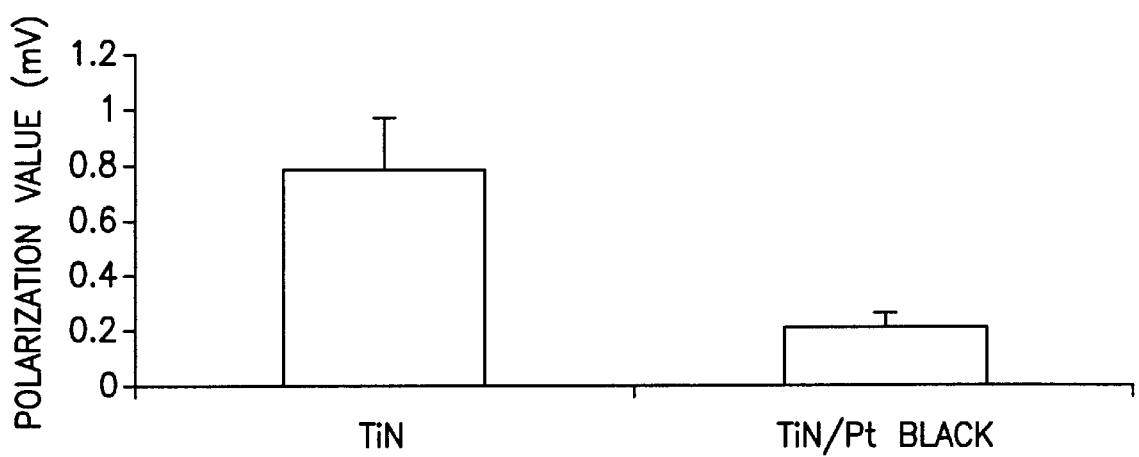
FIG. 5 is a graph comparing a stimulating electrode produced according to the invention with a conventional stimulating electrode.

Table 1 below and the graph of FIG. 5 depict the results achieved by the Example just presented.

TABLE 1

A COMPARISON OF POLARIZATION AMPLITUDES OF ASSEMBLED LEADS EMPLOYING A MATERIAL COATING OF PLATINUM BLACK and TITANIUM NITRIDE VERSUS A CONTROL, I.E. A MATERIAL COATING OF TITANIUM NITRIDE

| Sample Group | Polarization Value (mV) |
| --- | --- |
| TiN coated electrodes | 0.77 ± 0.18 |
| TiN/Pt Black coated electrodes | 0.19 ± 0.06 |

It should be understood that the foregoing description is only illustrative of the invention. Various alternatives and modifications can be devised by those skilled in the art without departing from the invention. Accordingly, the present invention is intended to embrace all such alternatives, modifications and variances, which fall within the scope of the appended claims.

What is claimed is:
1. An implantable stimulation lead, comprising:
   an electrical conductor extending between a proximal end and a distal end;
   an insulative sheath covering the conductor;
   an electrical connector coupled to the proximal end of the conductor for releasable attachment to a stimulating pulse generator;
   a distal electrode coupled to the distal end of the conductor and having a surface exposed through the exterior of the insulative sheath for directly contacting the endocardium of a patient's heart at the exposed surface;
   wherein substantially all of the exposed surface of the distal electrode is provided with an underlying layer of titanium nitride and an overlying layer of platinum black.
2. The implantable lead, as set forth in claim 1, wherein:
   the layer of titanium nitride on the distal electrode has a thickness of less than about 15 microns; and
   the layer of platinum black overlying the layer of titanium nitride has a thickness of less than about 15 microns.
3. The implantable lead, as set forth in claim 1, wherein:
   the polarization value exhibited by the distal electrode is held to a value of less than about 1 mV.
4. An implantable stimulating electrode having low polarization, comprising:
   a metallic substrate having an initially exposed outer surface substantially covered with a first inner layer of titanium nitride and a second outer layer of platinum black, the stimulating electrode exhibiting a polarization value of less than about 0.3 mV.
5. The implantable stimulating electrode, as set forth in claim 4, wherein:
   the first inner layer of titanium nitride has a thickness of less than about 15 microns; and
   the second outer layer of platinum black overlying the layer of titanium nitride has a thickness of less than about 15 microns.

* * * * *